(12) United States Patent
Rinner

(10) Patent No.: US 11,395,689 B2
(45) Date of Patent: Jul. 26, 2022

(54) SURGICAL RATCHETING ASSEMBLY

(71) Applicant: Precision Medical Industries, Inc., Rome City, IN (US)

(72) Inventor: James A. Rinner, Franksville, WI (US)

(73) Assignee: Precision Medical Industries, Inc., Rome City, IN (US)

( * ) Notice: Subject to any disclaimer, the term of this patent is extended or adjusted under 35 U.S.C. 154(b) by 442 days.

(21) Appl. No.: 16/417,175

(22) Filed: May 20, 2019

(65) Prior Publication Data

US 2019/0269448 A1 Sep. 5, 2019

Related U.S. Application Data

(63) Continuation of application No. 15/271,229, filed on Sep. 21, 2016, now Pat. No. 10,292,750.

(60) Provisional application No. 62/222,051, filed on Sep. 22, 2015.

(51) Int. Cl.
| | |
|---|---|
| *A61B 17/88* | (2006.01) |
| *A61B 90/00* | (2016.01) |
| *B25B 21/00* | (2006.01) |
| *B25B 13/46* | (2006.01) |
| *B25B 15/04* | (2006.01) |
| *A61B 17/00* | (2006.01) |

(52) U.S. Cl.
CPC .......... *A61B 17/8875* (2013.01); *A61B 90/08* (2016.02); *B25B 13/463* (2013.01); *B25B 15/04* (2013.01); *B25B 21/004* (2013.01); *A61B 2017/00407* (2013.01); *A61B 2017/00464* (2013.01); *A61B 2090/0813* (2016.02)

(58) Field of Classification Search
CPC .................................................. B25B 21/004
See application file for complete search history.

(56) References Cited

U.S. PATENT DOCUMENTS

| | | | | |
|---|---|---|---|---|
| 6,543,315 B2* | 4/2003 | Huang | .................. | B25B 13/463 |
| | | | | 192/43.2 |
| 6,658,970 B2* | 12/2003 | Shiao | .................... | B25B 13/468 |
| | | | | 192/43.1 |
| 7,062,994 B2* | 6/2006 | Chen | ...................... | B25B 13/463 |
| | | | | 81/62 |
| 7,168,342 B2* | 1/2007 | Gao | ...................... | B25B 13/463 |
| | | | | 81/58.4 |
| 8,485,068 B2* | 7/2013 | Campbell | ............ | B65D 75/322 |
| | | | | 81/62 |
| 8,544,365 B2* | 10/2013 | Wang | .................... | B25B 13/468 |
| | | | | 81/63.1 |

* cited by examiner

*Primary Examiner* — Hadi Shakeri
(74) *Attorney, Agent, or Firm* — Taylor IP, P.C.

(57) ABSTRACT

Disclosed are devices, systems and methods for improving medical instruments and related tools, such as a ratcheting module that can be attached to various surgical instruments used during surgery.

6 Claims, 6 Drawing Sheets

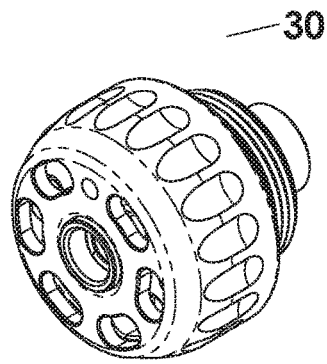
FIG. 29
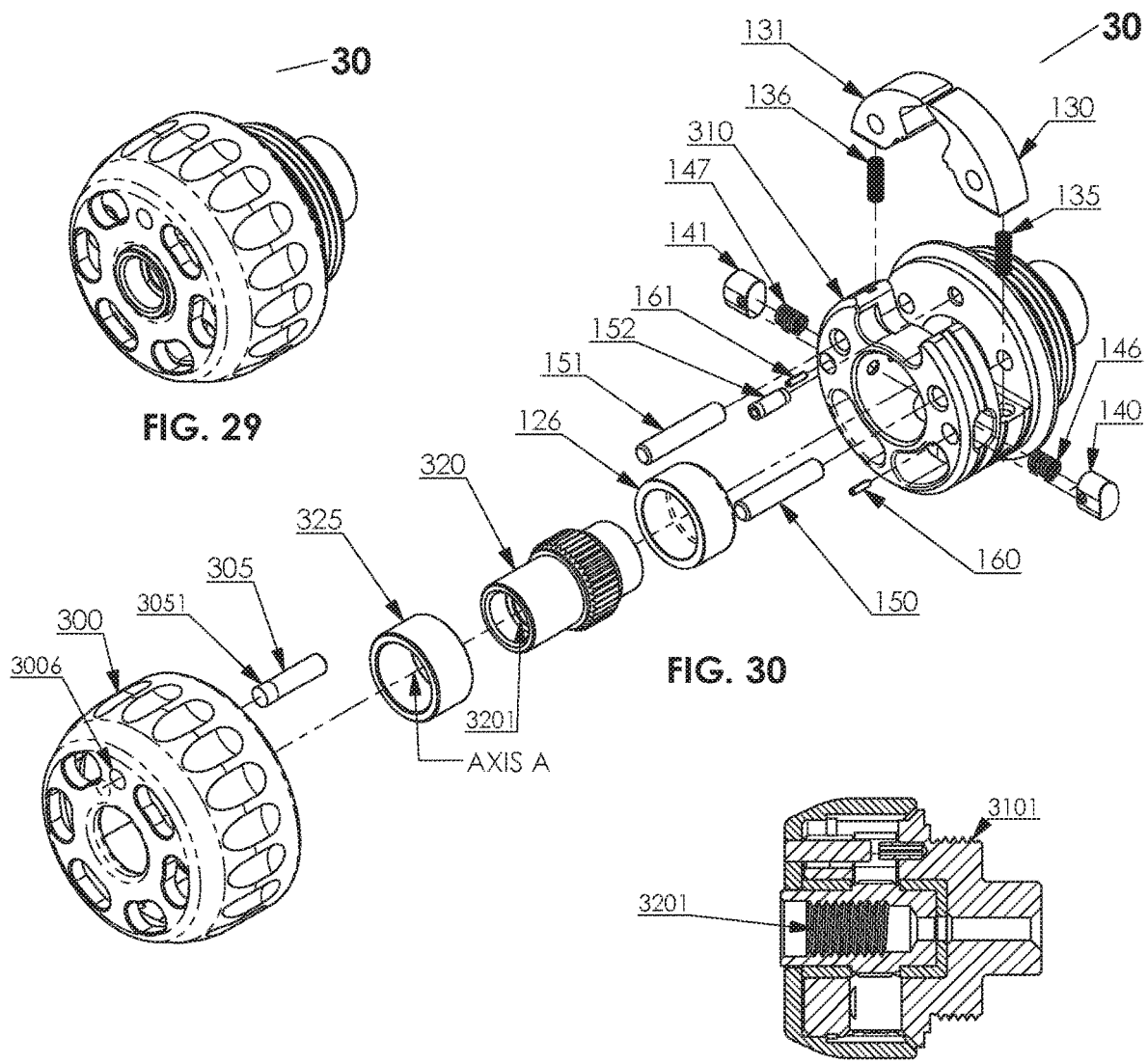
FIG. 30
FIG. 34
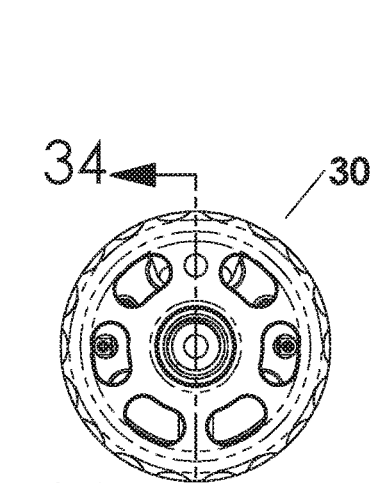
FIG. 31
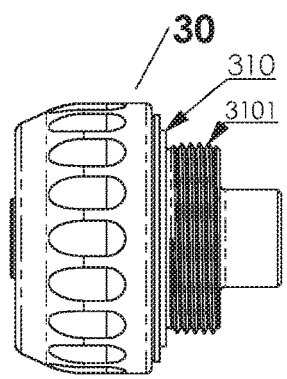
FIG. 32
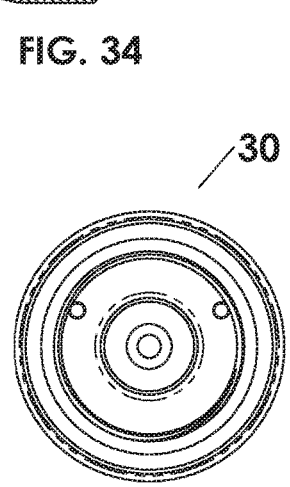
FIG. 33

SURGICAL RATCHETING ASSEMBLY

CROSS-REFERENCE TO RELATED APPLICATIONS

This application is a continuation of U.S. patent application Ser. No. 15/271,229, entitled "Ratcheting Module with Cleaning Ports," filed 21 Sep. 2016, which claims the benefit of U.S. Provisional Patent Application Ser. No. 62/222,051 entitled "Ratcheting Module with Cleaning Ports," filed Sep. 22, 2015, the disclosures of which are each incorporated by reference herein in their entireties.

TECHNICAL FIELD

Disclosed is a cleanable ratcheting module that is attached to various surgical instruments used during surgery. The cleaning is accomplished through various ports that allow for cleaning fluids to flow through the invention.

BACKGROUND OF THE INVENTION

Instruments used for inserting screws, drilling holes or revolving various implants or attachments have been used in the field of surgery for many years. Because instruments can contact and retain bodily fluids, fat, muscle and flesh it is important that they can be thoroughly cleaned of foreign matter. Typical ratcheting mechanisms cannot be easily taken apart for cleaning and are suspect to having bodily debris in the inner working mechanisms of the ratchet.

SUMMARY OF THE INVENTION

The present invention contains multiple cleaning fluid access ports on the distant end of the module with various channels through the device to aid in the proper flushing of cleaning fluids. This invention also has a unique selector blade mechanism that is used to position the ratcheting mechanism in various positions for clockwise, counter-clockwise and stationary driving methods while using unique features to secure the assembled mechanism. This same selector blade feature can also be easily positioned by the user to disassemble the mechanism for cleaning or maintenance.

BRIEF DESCRIPTION OF THE DRAWINGS

The present invention will be more understood in the detailed description and the accompanying drawings.

FIG. 29 depicts a front perspective view of embodiment 30 of the invention;

FIG. 30 depicts an exploded front perspective view of embodiment 30 of the invention;

FIG. 31 depicts a front planar view of the embodiment 30;

FIG. 32 depicts a side planar view of the embodiment 30;

FIG. 33 depicts a rear planar view of the embodiment 30; and

FIG. 34 is a sectional view of the area 34-34 shown in FIG. 31.

DETAILED DESCRIPTION OF THE DRAWINGS

In the following detailed description, for purposes of explanation, numerous specific details are set forth to provide a thorough understanding of the various embodiments of the disclosure. Those of ordinary skill in the art will realize that these various embodiments are illustrative only and are not intended to be limiting in any way. In addition, for clarity purposes, not all of the routine features of the embodiments described herein may be shown or described for every alternative embodiment. One of ordinary skill in the art would readily appreciate that in the development of any such actual implementation, numerous implementation-specific decisions may be required to achieve specific design objectives. These design objectives may vary from one implementation to another and from one developer to another, and the variations thereof are contemplated and included in the present disclosure.

Function

The intended use of the various embodiments of the Ratcheting Module is for driving, or rotating, a variety of surgical attachments in order to drill, thread, drive, rotate or place various implants or other instruments during surgery.

Components

Those of ordinary skill in the art should realize that the various embodiments described herein are illustrative only, are not intended to be limiting in any way and can be combined and subtracted to fit the specific needs during surgery.

Desirably, the overall dimensions and/or thickness or width and/or diameters of the invention (as well as the components of the invention) can be customized or particularized to an individual use.

Specifications

Figure 1:
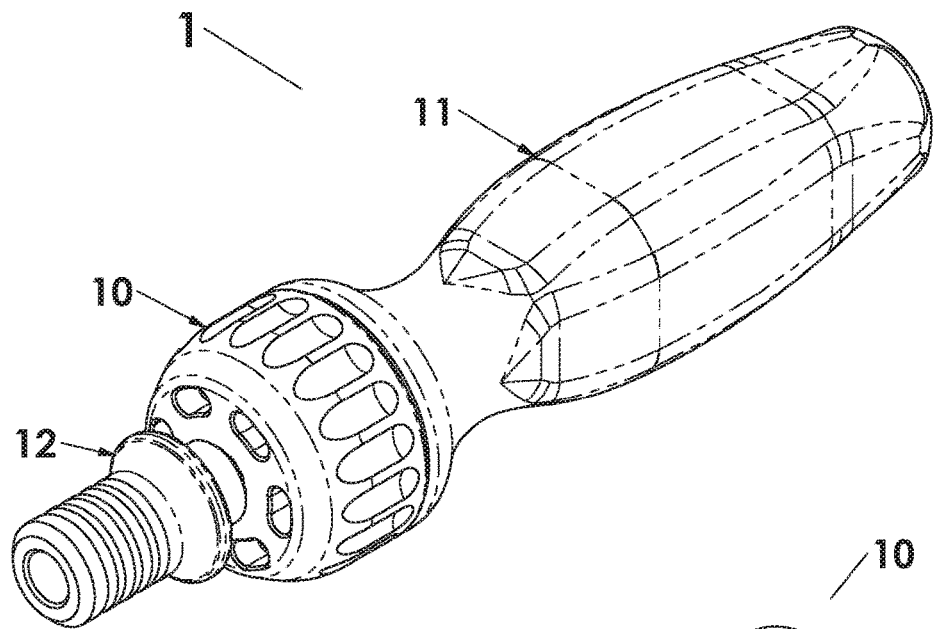
FIG. 1 depicts a front perspective view of the invention 10 with the addition of a generic Handle 11 and generic Tool Adapter 12.
Figure 2:
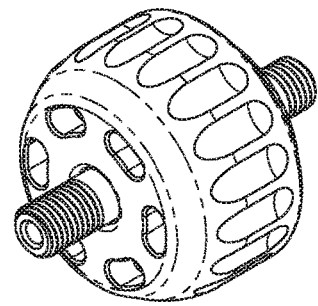
FIG. 2 depicts a front perspective view of the invention 10.
Figure 3:
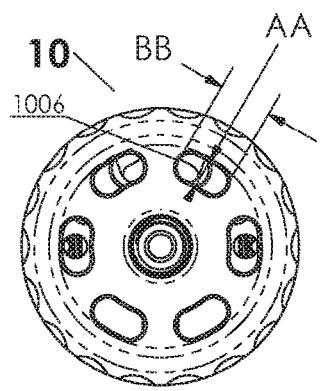
FIG. 3 depicts a front planar view of the invention 10.

FIG. 1 depicts a perspective view of one exemplary embodiment 1 of the invention 10 with a generic handle 11 attached at the rear of the invention 10 and a generic adapter mechanism 12 attached to the front of the invention 10.

Figure 4:
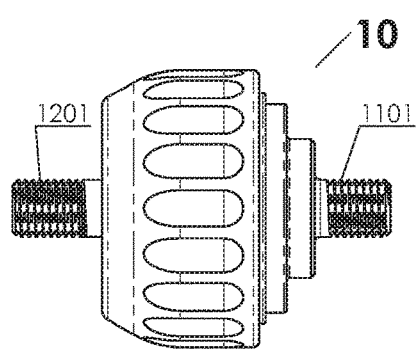
FIG. 4 depicts a side planar view of the invention 10.
Figure 5:
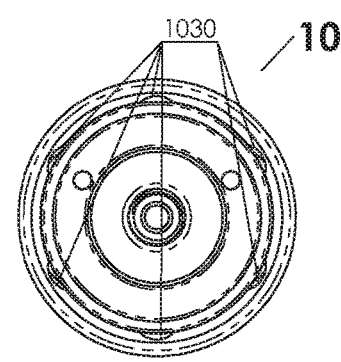
FIG. 5 depicts a rear planar view of the invention 10.

FIGS. 2-5 illustrate the overall shape of the invention 10. In FIG. 4 male threads 1101 and 1201 are shown and are used to attach various handles and adapters. Those skilled in the art know that these threads 1101 and 1201 can also be both female threads or one male and one female. Also those skilled in the art will know that instead of threads there could be press fits, tapers, welds, bonds or other known mechanisms of attachment used without departing from the nature of the invention. Those skilled in the art also know that instead of a handle 11 an attachment point to a powered source such as, but not limited to, an electric drill may also be used or instead of an adapter a direct attachment to a screwdriver, or other implements, may also be used without departing from the nature of the invention.

Figure 6:
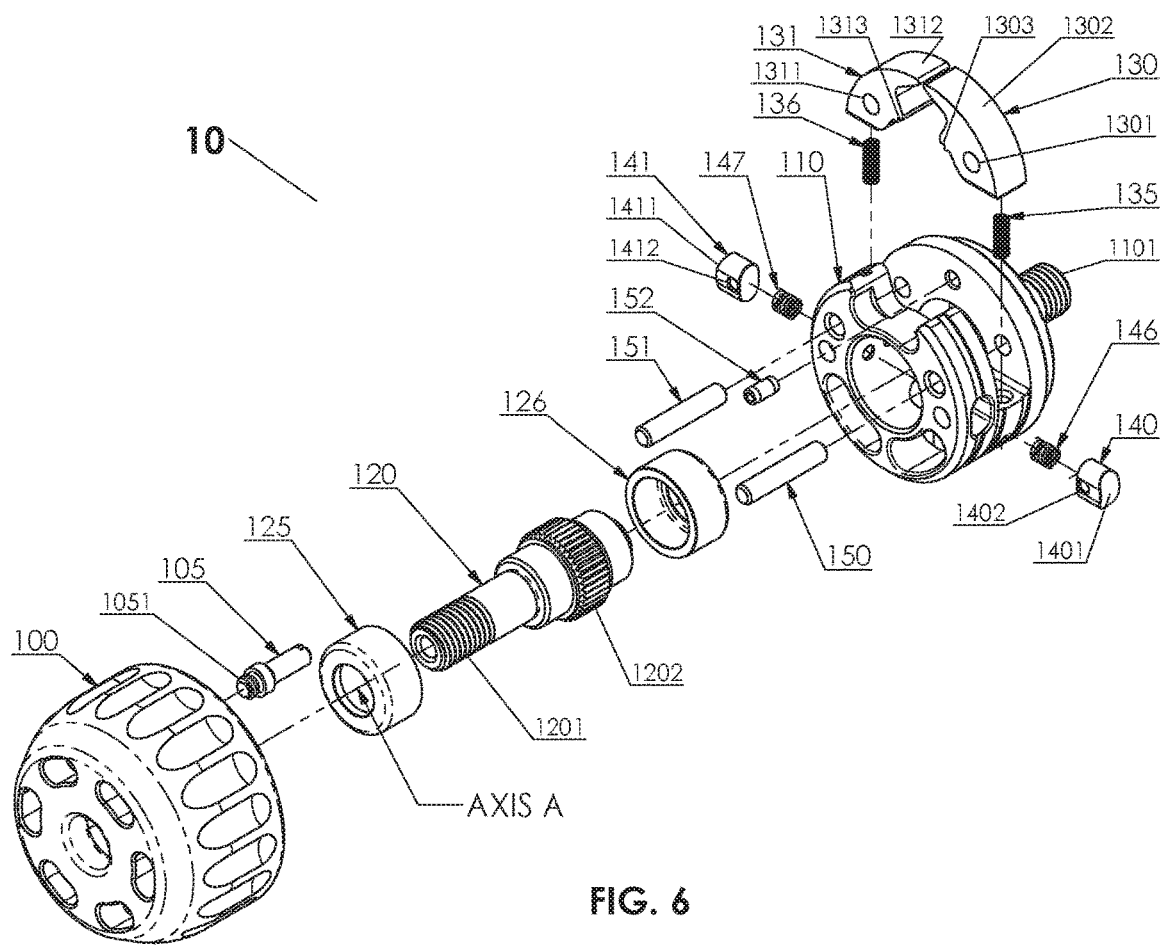
FIG. 6 depicts a exploded front perspective view of the invention 10.

FIG. 6 shows an exploded perspective view of the invention 10 and will be used, along with additional views to describe the operation of the invention. Though there are specific components described here those skilled in the art know that modification to the quantities or even the non-use of some of these components will not cause a departure from the nature of the invention. The Selector Pin 105 is attached to the Selector Cap 100 via a Male Thread 1051 and a female thread (not shown) in the Selector Cap (SEE FIG. 7). Those skilled in the art know that the Selector Pin 105 does not have to be threaded but could also be press fit, welded or even machined integrally on the Selector Cap 100.

Figure 8:
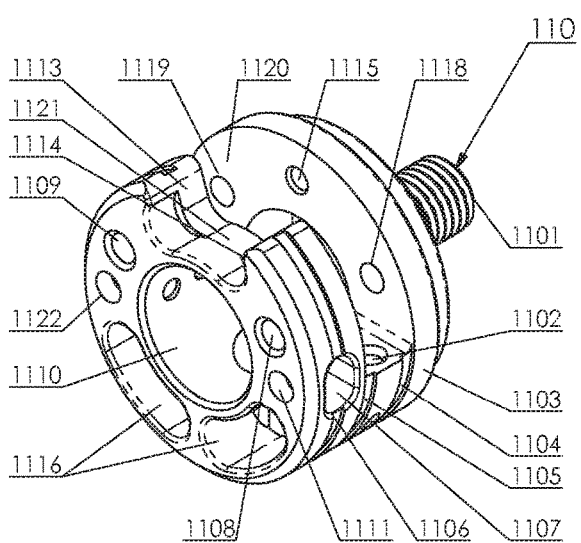
FIG. 8 front perspective view of the body 110.
Figure 9:
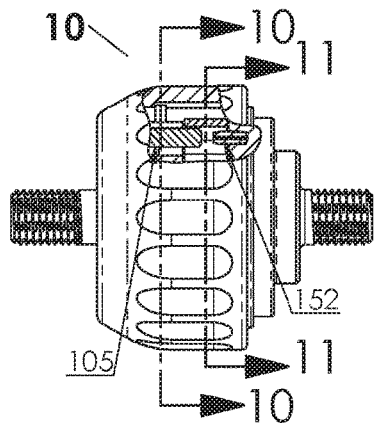
FIG. 9 is a side planar view of the invention 10 showing section lines 10-10 and 11-11.

FIG. 6 also shows a Body 110 that will contain various components of the invention 10. The Ratchet Shaft 120, along with the bearings 125 and 126 are placed into the bore 1110 (SEE FIG. 8) of the Body 110 and freely rotate in the clockwise or counter-clockwise motion. Though Bearings 125 and 126 are shown as one-piece items they can also be of ball bearing or needle bearing nature and can be made from various materials.

FIG. 6 further shows the Clockwise Ratcheting Pawl 130 and Counter-Clockwise Ratcheting Pawl 131 where the rotational motion around Axis A is determined when looking from the end of the male thread 1101 toward the male thread 1201 of the Ratchet Shaft 120. Description of how this ratcheting direction is accomplished is described later on in this document. Both the Ratcheting Pawls 130 and 131 are contained in channel 1120 of the Body 110 (SEE FIG. 8). The Ratcheting Pawls 130 and 131 are held in place by the Pawl Pins 150 and 151 respectively when the Pawl Pins 150 and 151 are inserted through the holes 1108 and 1109 then through the holes 1301 and 1311 of the Pawls 130 and 131 and finally into the holes 1118 and 1119 of the Body respectively. The male diameter of Pawl Pins 150 and 151 is smaller than the female diameters 1301 and 1311 of the Ratcheting Pawls 130 and 131 so that the Pawls can freely rotate around the Pins. Prior to the placement of the Pawls 130 and 131 the Pawl Springs 135 and 136 are placed into their respective Pawl Spring Holes 1102 (SEE FIG. 8). The Pawl Springs 135 and 136 apply pressure to the bottom of the Pawls to urgently move them forward to keep the Pawl Teeth 1303 and 1313 in spring pressure contact with the Ratchet Shaft Teeth 1202. Depending on the position of the Selector Cap 100 and Selector Pin 105 the spring pressure of the Pawl Springs 135 and 136 will also urgently move the Pawls forward to keep the Pawl Cam Surfaces 1302 and 1312 in contact with the Selector Pin 105. This will be further disclosed in the description of FIGS. 9-17. Also shown in FIGS. 6, 13, 14, 16 and 17 is the Pawl Stop Pin 152 which is placed in the Pawl Stop Pin Hole 1115 of the Body 110 (SEE FIG. 8) and is used to limit the motion of the Pawls 130 and 131 when being urged forward by the Pawl Springs 135 and 136 and there is no Ratchet Shaft 120 present which could occur during assembly, cleaning or maintenance.

FIG. 6 shows the Male Selector Blades 140 and 141, which are outwardly urged by Blade Springs 146 and 147 when all are placed into their respective Female Blade Slots 1106. A detailed description of their use will be explained further in this document when pertaining to FIGS. 9-25.

Figure 7:
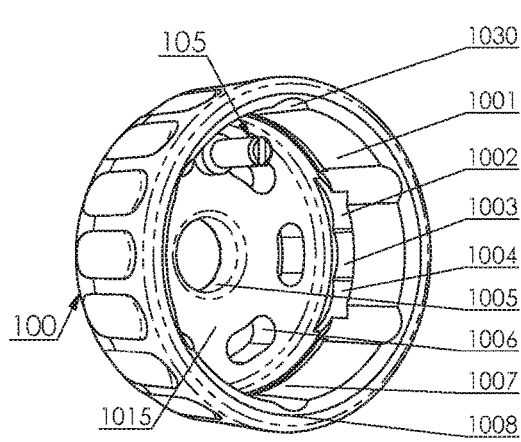
FIG. 7 depicts a rear perspective view of the selector cap 100 and Selector Pin 105 subassembly.

FIG. 7 depicts a perspective rear view of the subassembly consisting of the Selector Cap 100 and Selector Pin 105. As stated earlier in this document the pin can be attached in various manners such as, but not limited to, screw threads, welding, press fits or integral machining the pin to the cap in a one-piece construction. Shown in this view is the female diameter 1001 that mates with the male diameters 1103 of the Body 110. Also show are the Selector Blade Positional Surfaces 1002, 1003 and 1004; not shown in this view are the additional Selector Blade Positional Surfaces 1012, 1013 and 1014. Through the Surface 1015 of the Selector Cap 100 are the Hole Diameter 1005 which allows the Ratchet Shaft 120 to pass through and the Fluid Ports 1006. Though six are disclosed in this application the Fluid Ports 1006 can be any number and in various positions. Surface 1015 also secures the Ratchet Shaft 120 and Bearings 125 and 126 inside the Body 110. Other passages for the cleaning fluids to rinse the invention 10 are diameter 1007 and channels 1008 in the Selector Cap 100 and for the Body 110 (SEE FIG. 8) Ports 1111, 1122 and 1116, Channel 1121, and diameters 1104, 1105 and 1106. It is obvious to those skilled in the art to know that adding or subtracting from the number of or shape of diameters, ports and channels will not change the uniqueness of this invention.

Looking at FIGS. 18-21 you will see various views of a singular Selector Blade 140. The other Selector Blade 141 is identical so that the surfaces and features 1401, 1402 and 1403 of Selector Blade 140 are also featured on Selector Blade 141 and are numbered identically. With this in mind the Pawl Springs 135 and 136; Pawl Pins 150 and 151 and Selector Blade Springs 146 and 147 all have the same features as their counterpart. The male Oval Peripheries 1403 of Selector Blades 140 and 141 mates in the Female Oval Periphery 1107 of the Body 110. There is also a male or Convex Surface 1401 on the Selector Blade 140. This Convex Surface 1401 mates with the female or Concave Surfaces 1002, 1003 and 1004 of the Selector CAP 100 which are plainly seen in FIG. 23. Though the drawings of this invention show 2 sets of Selector Blades 140 and 141; and two sets of Concave Surfaces; 1002, 1003 and 1004 plus 1012, 1013 and 1014, one knowledgeable in the art understands that the function of the invention can be accomplished if there were only one Selector Blade and one set of Concave Surfaces, or more than two Selector Blades and Concave Sets.

Figure 10:
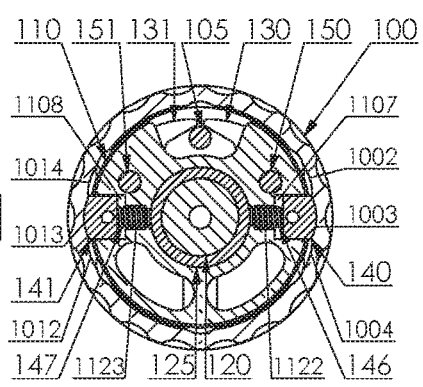
FIG. 10 is a sectional view of the area 10-10 shown in FIG. 9.
Figure 11:
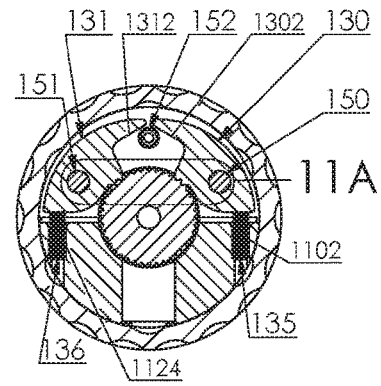
FIG. 11 is a sectional view of the area 11-11 shown in FIG. 9.
Figure 11A:
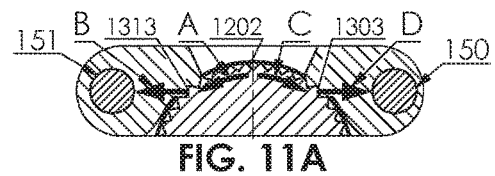
FIG. 11A is an enlarged sectional view of the area 11A shown in FIG. 11.
Figure 12:
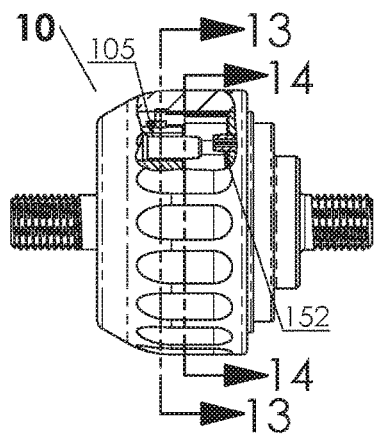
FIG. 12 is a side planar view of the invention 10 showing section lines 13-13 and 14-14.

FIGS. 9-11A depict the invention 10 in the neutral position where the invention does not allow the Ratchet Shaft 120 to ratchet or rotate. The section in FIG. 10 is defined by line 10-10 of FIG. 9 and is positioned so that the section slices in such a manner to show the Blade Springs 146 and 147, which are not sectioned for clarity. The section in FIG. 11 is defined by line 11-11 of FIG. 9 in such a manner to show the Pawl Springs 135 and 135, which are not sectioned for clarity. Note that this section does not go through the Selector Pin 105 so it is not viewable in FIG. 11. The limiter for the Ratchet Shaft 120 to rotate in the Body 110 is accomplished when the Selector Cap 100 is rotated around the Body 110 so that the Convex Surfaces 1401 of the Selector Blades 140 and 141 are nestled into the Concave Surfaces 1003 and 1013, respectively; in this position the Selector Pin 105 will be positioned between the cam surfaces 1302 and 1312 as seen in FIG. 10. When in this position the Pawl Springs 135 and 136 urge the Pawls 130 and 131 to rotate around the Pawl Pins 150 and 151 thus causing the Pawl Teeth 1303 and 1313 to enter the Ratchet Shaft Teeth 1202 of the Ratchet Shaft 120 (SEE FIG. 6). As shown in FIG. 11A The Ratchet Shaft 120 becomes stationary between the Pawls 130 and 131 and allows the user to turn the invention in both a clockwise or counter-clockwise motion with no ratcheting actions and thus having driving motion in either direction. When the Invention 10 Is rotated in either a clockwise or counter-clockwise motion as shown by Arrows A and B in FIG. 11A the Ratchet Shaft teeth 1202 apply a directional load as shown as Arrows B and D toward the Pawl Pins 150 or 151 and do not allow rotation of the Ratchet Shaft 120.

Figure 13:
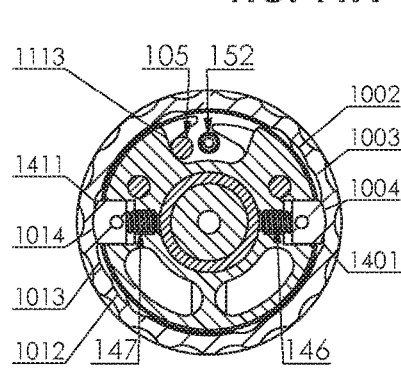
FIG. 13 is a sectional view of the area 13-13 shown in FIG. 12.
Figure 14:
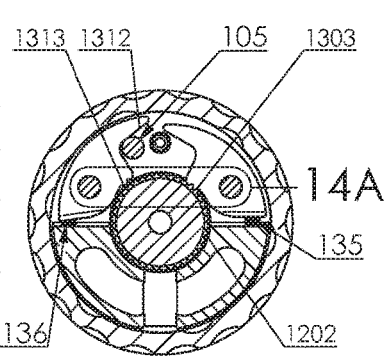
FIG. 14 is a sectional view of the area 14-14 shown in FIG. 12.
Figure 14A:
FIG. 14A is an enlarged sectional view of the area 14A shown in FIG. 14.

FIGS. 12-14A depict the invention 10 in the clockwise ratcheting position where the invention allows the Ratchet Shaft 120 to ratchet and rotate in a clockwise direction. The section in FIG. 13 is defined by line 13-13 of FIG. 12 and is positioned so that the section slices in such a manner to shown the Blade Springs 146 and 147, which are not sectioned for clarity. The section in FIG. 14 is defined by line 14-14 of FIG. 12 in such a manner to show the Selector Pin 105 interacting with the Cam Surface 1312 of the Counter-Clockwise Pawl 131. To prevent the Ratchet Shaft 120 to from rotating clockwise in the Body 110, the Selector Cap 100 is rotated around the Body 110 so that the Convex Surfaces 1401 of the Selector Blades 140 and 141 are nestled into the Concave Surfaces 1004 and 1014, respectively; in this position the Selector Pin 105 will be come in contact with cam surface 1312 of Counter-Clockwise Pawl 131 and cause the Pawl to rotate around Pawl Pin 151 and disengage the Pawl Teeth 1313 from the Ratchet Shaft Teeth 1202 as seen in FIG. 14 and FIG. 14A. The rotation of the Selector Cap 100 will cease when the Selector Pin 105 contacts surface 1113 of the Body 110. When in this position the Pawl Spring 135 continues to urge the Clockwise Pawl 130 to rotate around the Pawl Pin 150 thus causing the Pawl Teeth 1303 to enter the Ratchet Shaft Teeth 1202 of the Ratchet Shaft 120 in the same manner as described above in FIG. 11A. Because the Pawl Teeth 1313 of Counter-Clockwise Pawl 131 are removed from engagement with the Ratchet Shaft Teeth 1202 the Ratchet Shaft 120 is free to rotate in the direction shown by the Arrow D of FIG. 14A. Simultaneously with the rotation of the Ratchet Shaft 120, the Pawl teeth 1303 of Pawls 130 will rotate out of, or exit, the engagement with the Ratchet Shaft Teeth 1202 and continue until the apex of the Pawl Teeth 1303 passes the apex of the Ratchet Shaft Teeth 1202. When this occurs the Pawl Spring 135 will urge the Clockwise Pawl to rotate into and enter the Ratchet Shaft Teeth 1202. With continual rotation of the Ratchet Shaft 120 in the Arrow D direction the Clockwise Pawl will exit and enter the Ratchet Teeth 1303; this is known in the art as a ratcheting motion. However when the Ratchet Shaft 120 is turned in the Arrow C direction (SEE FIG. 11A) the Clockwise Pawl 130 will rotate in the ARROW G (SEE FIG. 14A) and the Pawl Teeth 1303 will enter into the Ratchet Shaft Teeth 1202. Then load will be applied in the direction of Arrow C in FIG. 11A and since the Ratchet Shaft teeth 1202 applies a directional load as shown as Arrow C toward the Pawl Pin 150 the combination will not allow rotation of the Ratchet Shaft 120.

Figure 15:
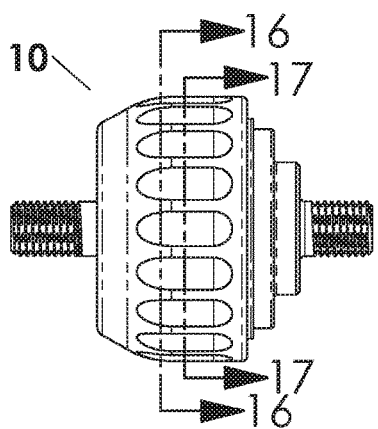
FIG. 15 is a side planar view of the invention 10 showing section lines 16-16 and 17-17.
Figure 16:
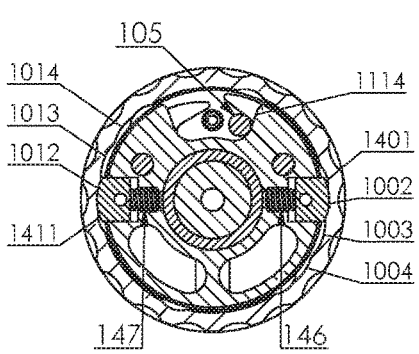
FIG. 16 is a sectional view of the area 16-16 shown in FIG. 15.
Figure 17:
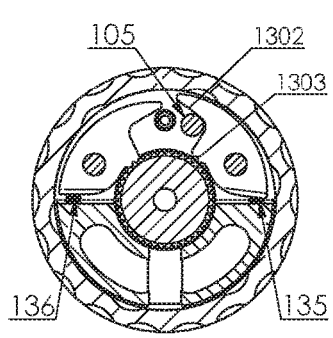
FIG. 17 is a sectional view of the area 17-17 shown in FIG. 15.
Figure 18:
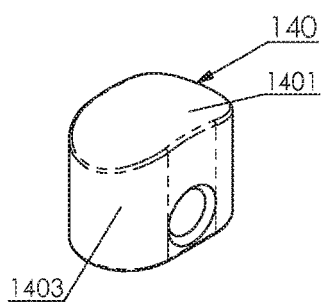
FIG. 18 depicts a perspective view of the Selector Blade 140.
Figure 19:
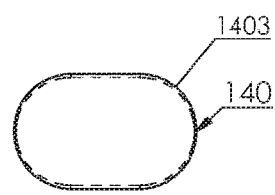
FIGS. 19-21 orthogonal views of the Selector Blade 140.

FIGS. 15-17 depict the invention 10 in the counter-clockwise ratcheting position where the invention allows the Ratchet Shaft 120 to ratchet and rotate in a counter-clockwise direction. The section in FIG. 16 is defined by line 16-16 of FIG. 15 and is positioned so that the section slices in such a manner to shown the Blade Springs 146 and 147, which are not sectioned for clarity. The section in FIG. 17 is defined by line 17-17 of FIG. 15 in such a manner to show the Selector Pin 105 interacting with the Cam Surface 1302 of the Clockwise Pawl 130. To prevent the Ratchet Shaft 120 from rotating counter-clockwise in the Body 110, the Selector Cap 100 is rotated around the Body 110 so that the Convex Surfaces 1401 of the Selector Blades 140 and 141 are nestled into the Concave Surfaces 1002 and 1012, respectively; in this position the Selector Pin 105 will come in contact with cam surface 1302 of Clockwise Pawl 130 and cause the Pawl to rotate around Pawl Pin 150 and disengage the Pawl Teeth 1303 from the Ratchet Shaft Teeth 1202 as seen in FIG. 17. The rotation of the Selector Cap 100 will cease when the Selector Pin 105 contacts surface 1114 of the Body 110. When in this position the Pawl Spring 136 continues to urge the Counter-Clockwise Pawl 131 to rotate around the Pawl Pin 151 thus causing the Pawl Teeth 1313 to enter the Ratchet Shaft Teeth 1202 of the Ratchet Shaft 120 in the same manner as described above in FIG. 11A. The Ratchet Pawls 130 and 131 are mirrored the description for interaction of the components with each is described above, only mirrored.

Figure 22:
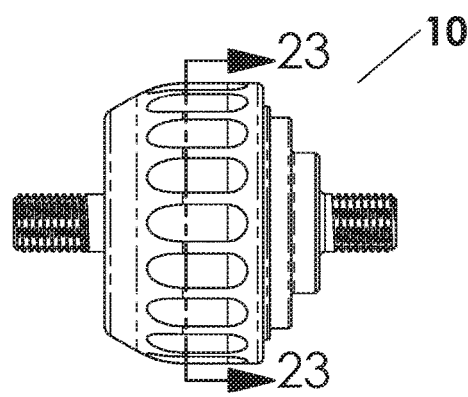
FIG. 22 is a side planar view of the invention 10 showing section line 23-23.
Figure 20:
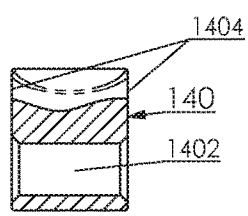
Figure 21:
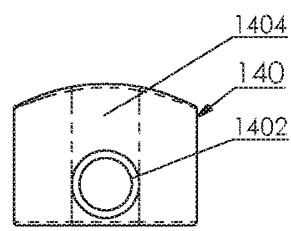
Figure 23:
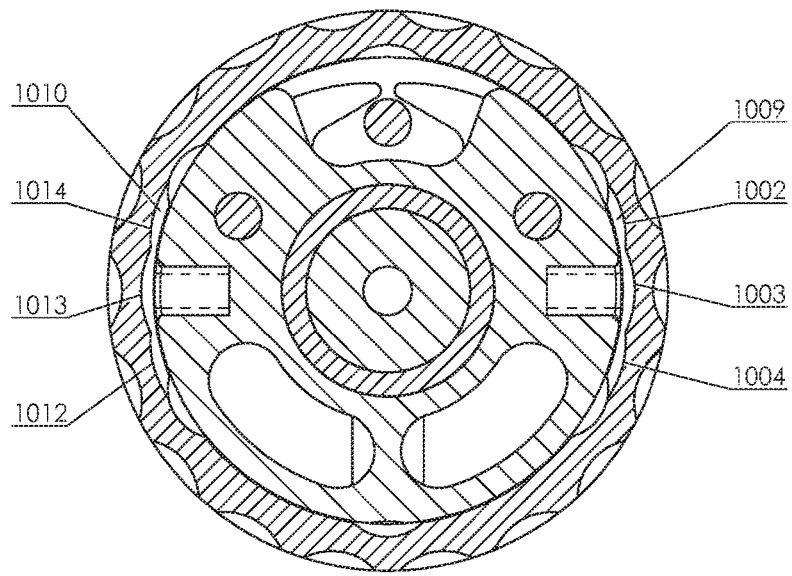
FIG. 23 is an enlarged sectional view of the area 23-23 shown in FIG. 22.
Figure 24:
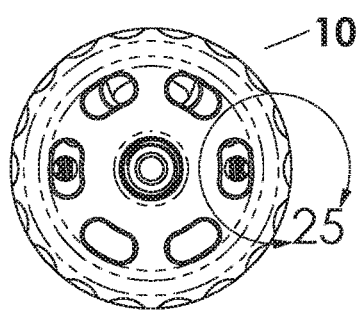
FIG. 24 depicts a front planar view of the invention 10 and area 25.
Figure 25:
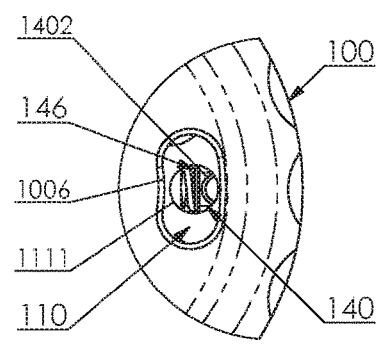
FIG. 25 depicts an enlarged view of the area 25 shown in FIG. 24.

FIGS. 18-25 depict an additional use of the Selector Blades 140 and 141 where they are used to retain Selector Cap Subassembly (Selector Cap 100 and Selector Pin 105) and the Ratchet Shaft Subassembly (Ratchet Shaft 120, Bearing 125 and Bearing 126). FIG. 22 contains section line 23-23 so that the features of the Concave Surfaces 1002, 1003, 1004, 1012, 1013 and 1014 are clearly discerned in FIG. 23. Also shown in FIG. 23 are the Retention Surfaces 1009 and 1010 which, in conjunction with the planar areas 1404 of the Selector Blades, are used to retain the Selector Cap Subassembly and Ratchet Shaft Subassembly. In order to accomplish this retention the components described earlier are assembled into the Body 110 and the Blade Springs are compressed by applying pressure to the Selector Blades 140 and 14. Then the selector cap subassembly consisting of the Selector Cap 100 and Selector Pin 105 is placed over the Body 110 subassembly till the spring urged Selector Blades 140 and 141 pass the planar Retention Surfaces 1009 and 1010. When in this position the Blade Springs will force the Selector Blades 140 and 141 into the recessed areas of 1002, 1003, 1004, 1009, 1010, 1012, 1013 and 1014 thus retaining the Selector Cap Subassembly and Ratchet Shaft Subassembly in place. To remove the Selector Cap Subassembly and Ratchet Shaft Subassembly a tool can be used through the Ports 1006, 1111 and 1122 and into the Blade Holes 1402 to move the Selector Blades 140 and 141 inwardly while compressing the Blade Springs 146 and 147 thus moving the Selector Blades 140 and 141 past the Retention Surfaces 1009 and 1010. This access can be seen in FIGS. 24 and 25.

Figure 26:
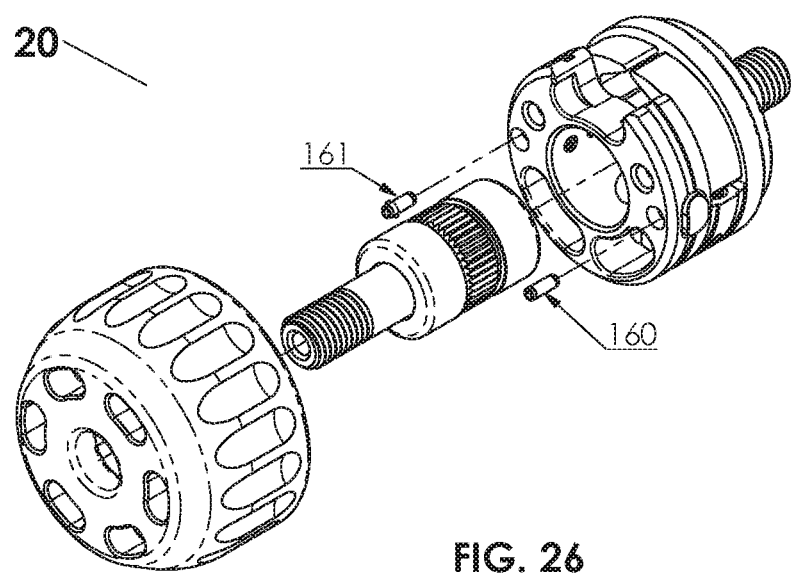
FIG. 26 depicts a exploded front perspective view of embodiment 20 of the invention.
Figure 27:
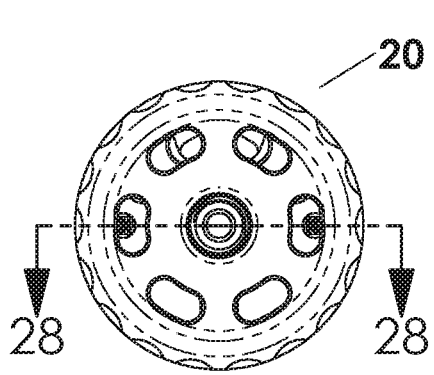
FIG. 27 depicts a front planar view of the embodiment 20 showing section lines 28-28.
Figure 28:
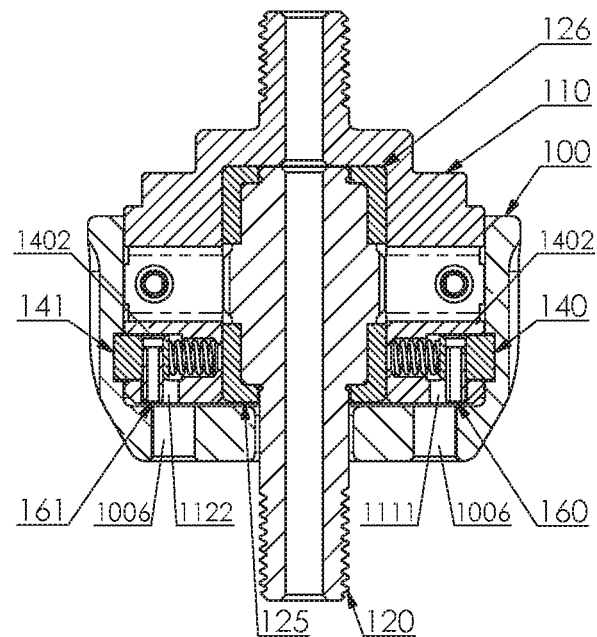
FIG. 28 is a sectional view of the area 28-28 shown in FIG. 27.

FIGS. 26-28 show an additional embodiment 20 of the invention is shown where the Selector Blades 140 and 141 plus the Blade Springs 146 and 147 are retained in the Body 110 so that there are no loose parts which could be lost during various of assembly, disassembly, cleaning or maintenance. This is accomplished through the use of Blade Pins 160 and 161 that are inserted, and held into position by various means known by those skilled in the art, into the Blade Holes 1402. When the Blade Pins 160 and 161 are in place in the Blades the Ports 1111 and 1122 limit the travel of the Blades 140 and 141 thus retaining them in the Body 110. The Ports 1111 and 1122 are positioned and of sufficient size to allow full movement of the Selector Blades 140 and 141. To remove the Selector Cap Subassembly and Ratchet Shaft Subassembly simply follow the same steps described earlier in this document.

FIGS. 29-34 show an additional embodiment 30 where the body 310 incorporates a larger male thread 3101 for attachment to a handle similar to Handle 11 of FIG. 1. The Ratchet Shaft 320 has a Female Thread 3201 for accepting adapters similar to generic adapter mechanism 12 but has a male thread that mates with the Female Thread 3201. As mentioned above, where the Selector Pin 105 can be attached to the Selector Cap 100 in various manners, the Selector Pin 305 may be friction fit into the Selector Pin Hole 3006 of the Selector Cap 300.

Various features of the present invention are unlike prior art ratcheting mechanisms. While most prior art ratcheting mechanisms use a single spring urged shaft. For example, the device depicted in GAO (U.S. Pat. No. 8,109,181) includes a spring urged shaft 42 which locates into various small detents 44 and 46 for selecting ratchet directions. Other designs use a spring urged detent, such as depicted in Gauthier (U.S. Pat. No. 6,817,458), where the spring urged detent 82 engages into small depressions 80 for the selection of ratcheting directions. Still other designs employ a spring urged spherical ball, such as depicted in Herman (U.S. Pat. No. 4,777,852), where a spring urged ball 89 mates into the small semi-circular recesses 97a, 97b and 97c. In contrast, at least one exemplary embodiment of the present invention utilizes one or two Selector Blades 140 and 141, that mate in the large Selector Blade Positional Surfaces 1002, 1003, 1004, 1012, 1013 and 1014. This embodiment of the invention desirably retains the Selector Cap 100 or 300 in place through the surfaces 1404 of the Selector Blades 140 and 141 coming into contact with the Retention Surfaces 1009 and 1010 as shown in FIG. 23 (and in various embodiments these forces retaining the cap desirably act along a line of action perpendicular to the line of action of the spring force). This Selector Cap arrangement and retention is unique to this invention, for at least the reason that additional features and components like the screws 64 of the GAO patent are required by other designs, and/or the retention ring 84 of the Gauthier patent and/or the retention ring 105 of the Herman patent are required to keep the ratcheting mechanism assembled. The invention also has a unique feature of using the Selector blades to not only keep the Selector Cap in the desired position, but also retain the cap on the mechanism.

A further unique feature of the Selector Blades and related components is that the disclosed device in the present invention can be disassembled easily by moving the Selector Blades toward AXIS A and disengaging the Selector Blades from the Selector Blade Positional Surfaces and Retention Surfaces by placing a tool through the Fluid Ports 1006 (SEE FIGS. 26, 27 and 28) in the Selector Cap, and attaching it to the Selector Blade Stop Pins 160 and 161, then moving the tool toward the AXIS A. The holes 1111 and 1122 are designed for such movement while also retaining the Selector Blades, Springs and Pin in a captured position so there are desirably no loose components once assembled and/or disassembled.

Moreover, because of size restrictions in prior art devices, such devices typically use a small spring, made from a large diameter wire, to retain the cap in the desired selected position. Many times the spring must be compressed to its higher limits, close to or even pass, the recommended load limits of the material. During repeated use a prior art spring will often fatigue and loose spring pressure. These small springs also undergo repeated high temperature sterilization cycles which could further shorten the life of the spring. Because the surface 1401 of the Selector Blade 140 and the mating Selector Blade Positional Surfaces in the present embodiment can be made much larger than the semi-circular or depressions in the prior art, the spring load required to hold the Selector Cap in the desired location in the disclosed devices is reduced so the Selector Blade Springs 1122 and 1123 can be made to work in a range that insures a long life.

The invention also is unique in that it allows for cleaning of the internal mechanisms of the ratchet without disassembly of the components by allowing cleaning fluid to flow through the multiple Fluid Ports 1006 of the Selector Cap 100 (SEE FIG. 7); then through the multiple Fluid Grooves 1030 of the Selector Cap 100; then through the Body Ports 1111, 1122, 1122 and 1116; then through Body Diameters 1104, 1105 and 1106 and the fluid can then exit through the multiple Fluid Grooves 1030 (SEE FIG. 5) near the generic handle 11. The multiple Fluid Ports 106 are, in one exemplary embodiment, at least 2.5 mm wide (AA of FIG. 3) and 6 mm long (BB of FIG. B), such that a sufficient amount of cleaning fluid can enter the ratcheting mechanism to thoroughly rinse the mechanism of debris and body fluids that have entered the ratchet during surgery.

Various embodiments of the present invention also incorporate through holes behind every spring to desirably insure a pathway for the fluid to drain and not be trapped in the mechanism. See FIG. 25 where it can be seen that, for virtually any orientation of the device and/or positioning of the Selector Blade 110, there is direct access via hole 1111 for the insertion and removal of the cleaning fluids. The multiple Fluid Ports, holes and grooves desirably allow the cleaning fluid to drain from the ratcheting mechanism, regardless of the position, or orientation, it is placed in after cleaning. In various embodiments, ports such as those described herein can desirably be sized, shaped and/or otherwise arranged to allow for passage of cleaning fluids and/or gases, without being large enough and/or positioned to allow larger particles of anatomical debris from prior surgeries to enter and/or jam the ratcheting mechanism.

Alternative Configurations

The various components described herein may be formed in a variety of shapes, sizes and/or configurations. For example, the embodiments 10 and 20 may be formed in a variety of shapes and configurations, which will desirably facilitate the use of various shaped Handles 11 and Tool Adapters 12. Similarly, the various features described herein could include features that are unique to specific attachments without departing from the spirit or essential character of the invention.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing inventions have been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

What is claimed is:

1. A surgical ratchet assembly having a proximal handle attachment point and a distal driver attachment point, a ratcheting mechanism located between the proximal handle attachment point and the distal driver attachment point, and a rotatable selector cap having an interior space which substantially surrounds the ratcheting mechanism, the rotatable selector cap comprising a generally cylindrical ring portion and a distal wall portion, wherein the rotatable selector cap can be selectively rotated to at least one of a first selector position, a second selector position and a third selector position, such that when the rotatable selector cap is rotated to the first selector position, rotation of the proximal handle in a clockwise direction will drive the distal driver attachment point in the clockwise direction and rotation of the proximal handle in a counter clockwise direction will ratchet the proximal handle relative to the distal driver attachment point, when the rotatable selector cap is rotated to the second selector position, rotation of the proximal handle in the clockwise direction will drive the distal driver attachment point in the clockwise direction and rotation of the proximal handle in the counter clockwise direction will drive the distal driver attachment point in the counter clockwise direction, and when the rotatable selector cap is rotated to the third selector position, rotation of the proximal handle in the clockwise direction will ratchet the proximal handle relative to the distal driver attachment point and rotation of the proximal handle in the counter clockwise direction will drive the distal driver attachment point in the counter clockwise direction, wherein the generally cylindrical ring portion of the rotatable selector cap defines at least one retention groove which extends in a circumferential direction and is configured for matingly receiving therein a single spring loaded retention member so as to retain the rotatable selector cap in a desired position relative to the ratcheting mechanism, wherein the surgical ratchet assembly further comprises a selector pin attached to the rotatable selector cap, at least a portion of the selector pin extending into the ratcheting mechanism and selectively engaging and disengaging with a cam surface of at least one pawl of the ratcheting mechanism, the ratcheting mechanism including a pawl stop pin that is substantially cylindrical and is configured for limiting a rotational motion of the at least one pawl.

2. The surgical ratchet assembly of claim 1, further comprising at least one of the spring loaded retention member extending outward from an axially extending opening formed in the ratcheting mechanism, at least a portion of an outer surface of the spring loaded retention member extending into a corresponding one of the retention groove formed into an inner wall of the generally cylindrical ring portion of the rotatable selector cap, the retention groove including a retention surface that engages with the portion of the outer surface to retain the rotatable selector cap in the desired position, which is a desired longitudinal position, relative to the ratcheting mechanism and allow the rotatable selector cap to rotate relative to the ratcheting mechanism along a path defined by the retention groove.

3. The surgical ratchet assembly of claim 1, further comprising at least one of the spring loaded retention member extending outward from an axially extending opening formed in the ratcheting mechanism, at least a portion of the spring loaded retention member extending into a corresponding one of the retention groove formed into an inner wall of the generally cylindrical ring portion of the rotatable selector cap, the retention groove engaging with a portion of the spring loaded retention member to retain the rotatable selector cap in the desired position, which is a desired longitudinal position, relative to the ratcheting mechanism, wherein the interaction between the spring loaded retention member and the retention groove defines a plurality of rotational positions of the rotatable selector cap relative to the ratcheting mechanism.

4. The surgical ratchet assembly of claim 1, further comprising the spring loaded retention member, which is matingly received by the at least one retention groove so as to retain the single spring-loaded retention member therein and thereby to inhibit both a circumferential movement and an axial movement of the single spring-loaded retention member relative to the at least one retention groove.

5. The surgical ratchet assembly of claim 4, further comprising two of the at least one spring loaded retention member, wherein the rotatable selector cap includes six of the at least one retention groove, the rotatable selector cap including a first circumferential side and a second circumferential side opposing the first circumferential side, three of the at least one retention groove being disposed on the first circumferential side of the rotatable selector cap and being adjacent to one another in an end-to-end fashion, and three of the at least one retention groove being disposed on the second circumferential side of the rotatable selector cap and being adjacent to one another in the end-to-end fashion, each of the at least one retention groove being configured for receiving therein a respective one of the spring-loaded retention member.

6. The surgical ratchet assembly of claim 1, wherein the selector pin is substantially cylindrical and extends parallel to an axis of rotation of the surgical ratchet assembly.

* * * * *